(12) United States Patent
Harrison

(10) Patent No.: US 11,185,555 B2
(45) Date of Patent: Nov. 30, 2021

(54) METHOD TO KILL PATHOGENIC MICROBES IN A PATIENT

(71) Applicant: Noah James Harrison, Huntington Beach, CA (US)

(72) Inventor: Noah James Harrison, Huntington Beach, CA (US)

(*) Notice: Subject to any disclaimer, the term of this patent is extended or adjusted under 35 U.S.C. 154(b) by 0 days.

(21) Appl. No.: 15/096,214

(22) Filed: Apr. 11, 2016

(65) Prior Publication Data
US 2016/0220700 A1 Aug. 4, 2016

(51) Int. Cl.
| | |
|---|---|
| C12N 15/86 | (2006.01) |
| C12N 15/85 | (2006.01) |
| A61K 31/711 | (2006.01) |
| A61K 38/00 | (2006.01) |
| C12N 7/01 | (2006.01) |
| A61K 31/513 | (2006.01) |
| A61K 31/7048 | (2006.01) |
| A61K 31/4709 | (2006.01) |
| A61K 31/65 | (2006.01) |
| A61K 31/7052 | (2006.01) |
| A61K 31/422 | (2006.01) |
| A61K 45/06 | (2006.01) |
| A61K 9/00 | (2006.01) |

(52) U.S. Cl.
CPC ........ *A61K 31/7048* (2013.01); *A61K 31/422* (2013.01); *A61K 31/4709* (2013.01); *A61K 31/513* (2013.01); *A61K 31/65* (2013.01); *A61K 31/7052* (2013.01); *A61K 45/06* (2013.01); *C12N 15/86* (2013.01); *A61K 9/0019* (2013.01); *A61K 38/00* (2013.01); *C12N 2710/10343* (2013.01); *C12N 2740/16043* (2013.01); *C12N 2750/14143* (2013.01); *C12N 2770/36143* (2013.01); *C12N 2830/008* (2013.01)

(58) Field of Classification Search
None
See application file for complete search history.

(56) References Cited

U.S. PATENT DOCUMENTS

| | | |
|---|---|---|
| 5,658,565 A | 8/1997 | Billiar et al. |
| 5,770,576 A | 6/1998 | Morozov et al. |
| 5,872,104 A | 2/1999 | Vermeulen et al. |
| 6,140,306 A | 10/2000 | Lambert, Jr. et al. |
| 6,410,041 B1 | 6/2002 | Lewis et al. |
| 6,503,881 B2 | 1/2003 | Krieger et al. |
| 6,685,935 B1 | 2/2004 | Pawelek et al. |
| 6,727,078 B2 | 4/2004 | Montelaro et al. |
| 6,759,229 B2 | 7/2004 | Schaak |
| 6,875,439 B2 | 4/2005 | Lewis et al. |
| 7,125,541 B2 | 10/2006 | Thorpe et al. |
| 7,223,740 B2 | 5/2007 | Visser et al. |
| 7,285,276 B2 | 10/2007 | Murdin et al. |
| 7,323,179 B2 | 1/2008 | Balaban |
| 7,348,161 B2 | 3/2008 | Gay et al. |
| 7,402,066 B2 | 7/2008 | Fischetti et al. |
| 7,405,066 B2 | 7/2008 | Holland et al. |
| 7,622,300 B2 | 11/2009 | Kappes et al. |
| 7,682,828 B2 | 3/2010 | Jaenisch et al. |
| 7,709,224 B2 | 5/2010 | Fang et al. |
| 7,781,214 B2 | 8/2010 | Smith et al. |
| 7,919,601 B2 | 4/2011 | Ramadugu et al. |
| 7,923,243 B2 | 4/2011 | Lee |
| 7,960,518 B2 | 6/2011 | Throsby et al. |
| 7,985,729 B2 | 7/2011 | Lim et al. |
| 8,003,779 B2 | 8/2011 | Kyrkanides |
| 8,043,624 B2 | 10/2011 | Pillich et al. |
| 8,236,527 B2 | 8/2012 | Chen et al. |
| 8,277,816 B2 | 10/2012 | Yusibov et al. |
| 8,388,946 B2 | 3/2013 | Soothill et al. |
| 8,445,639 B2 | 5/2013 | Scholl et al. |
| 8,557,575 B2 | 10/2013 | Dessain et al. |
| 8,591,862 B2 | 11/2013 | Brahmbhatt et al. |
| 8,642,040 B2 | 2/2014 | Mi et al. |
| 8,652,465 B2 | 2/2014 | Freeman et al. |
| 8,669,263 B2 | 3/2014 | Lemke et al. |
| 8,691,529 B2 | 4/2014 | Berger |
| 8,691,963 B2 | 4/2014 | Brahmbhatt et al. |
| 8,734,803 B2 | 5/2014 | Yusibov et al. |
| 8,765,470 B2 | 7/2014 | Thomson et al. |
| 8,778,899 B2 | 7/2014 | Ferber |
| 8,802,387 B2 | 8/2014 | King et al. |
| 8,821,856 B2 | 9/2014 | Baltimore et al. |
| 8,829,173 B2 | 9/2014 | Gruber et al. |
| 8,865,158 B2 | 10/2014 | Qimron et al. |
| 8,894,994 B2 | 11/2014 | Koski et al. |
| 8,900,597 B2 | 12/2014 | Anderson et al. |
| 8,956,864 B2 | 2/2015 | Brahmbhatt et al. |
| 8,986,697 B2 | 3/2015 | Ma et al. |

(Continued)

OTHER PUBLICATIONS

Pappas, Species on Earth. Life Sci, May 2016.*
Konduru et al. Virol J 2008;15:155, pp. 1-9.*
Yang et al. Vet Human Toxicol 1996;38:107-112.*
Russell et al. J Virol 2003;77:5801-5809.*
Bento et al. BMC Biotech 2004;4:29, pp. 1-10.*
Davies et al. Microbiol Mole Biol Rev 2010;74:417-33.*
Van Hoek et al. Frontier in Microbiol 2011 ;2:203, pp. 1-27.*
Peyton et al. Curr Topics Med Chem 2012;12:400-7.*
Ni et al. Adv Drug Deliv Rev 2016;106(Pt A):3-26.*

(Continued)

*Primary Examiner* — Maria Marvich
(74) *Attorney, Agent, or Firm* — Barcelo, Harrison & Walker, LLP

(57) ABSTRACT

An improved method to kill pathogenic microbes in a patient is disclosed and claimed. The improved method includes transducing eukaryotic cells of the patient with a first viral vector that will not transfect the pathogenic microbes. The first viral vector is replication defective and encodes in its recombinant genome a first antimicrobial resistance gene and a promoter. An antimicrobial medication is administered to the patient.

29 Claims, 4 Drawing Sheets

(56) References Cited

U.S. PATENT DOCUMENTS

| | | |
|---|---|---|
| 9,034,602 B2 | 5/2015 | Koski et al. |
| 9,066,982 B2 | 6/2015 | Brahmbhatt et al. |
| 9,068,159 B2 | 6/2015 | Holland et al. |
| 9,133,481 B2 | 9/2015 | Bovolenta et al. |
| 9,145,559 B2 | 9/2015 | Shaul et al. |
| 9,149,536 B2 | 10/2015 | Baasov et al. |
| 9,242,007 B2 | 1/2016 | Brahmbhatt et al. |
| 9,267,140 B2 | 2/2016 | Baltimore et al. |
| 9,301,996 B2 | 4/2016 | Koski et al. |
| 9,328,146 B2 | 5/2016 | Charneau et al. |
| 2002/0044922 A1 | 4/2002 | Mardh |
| 2002/0150556 A1 | 10/2002 | Vile et al. |
| 2003/0147852 A1 | 8/2003 | Schaak |
| 2003/0166030 A1 | 9/2003 | O'Toole et al. |
| 2003/0166595 A1 | 9/2003 | Von Lintig et al. |
| 2003/0175246 A1 | 9/2003 | Schaak |
| 2005/0004030 A1 | 1/2005 | Fischetti et al. |
| 2006/0140911 A1 | 6/2006 | Sharp et al. |
| 2006/0292135 A1 | 12/2006 | Loomis et al. |
| 2008/0020441 A1 | 1/2008 | Brahmbhatt et al. |
| 2008/0188436 A1 | 8/2008 | Brahmbhatt et al. |
| 2008/0226601 A1 | 9/2008 | Federoff et al. |
| 2009/0311234 A1 | 12/2009 | Koski et al. |
| 2011/0136688 A1 | 6/2011 | Scholl et al. |
| 2011/0209228 A1 | 8/2011 | Cocks et al. |
| 2012/0172292 A1 | 7/2012 | Nudler et al. |
| 2013/0149330 A1 | 6/2013 | Deisseroth |
| 2013/0195800 A1 | 8/2013 | Roeth et al. |
| 2013/0216622 A1 | 8/2013 | Koski et al. |
| 2013/0315869 A1 | 11/2013 | Qimron et al. |
| 2014/0004602 A1 | 1/2014 | Weel-Sneve et al. |
| 2014/0127785 A1 | 5/2014 | Koski et al. |
| 2014/0294826 A1 | 10/2014 | Shoemaker |
| 2014/0308367 A1 | 10/2014 | Collins et al. |
| 2014/0314754 A1 | 10/2014 | Yusibov et al. |
| 2014/0356395 A1 | 12/2014 | Barry |
| 2014/0370495 A1 | 12/2014 | Jacobs et al. |
| 2015/0056178 A1 | 2/2015 | Koski et al. |
| 2015/0174130 A1 | 6/2015 | Skaar et al. |
| 2015/0209418 A1 | 7/2015 | Koski et al. |
| 2015/0307495 A1 | 10/2015 | Striker et al. |
| 2016/0017295 A1 | 1/2016 | Schaffer et al. |
| 2016/0038572 A1 | 2/2016 | Nelson |
| 2016/0068917 A1 | 3/2016 | Chiu et al. |
| 2016/0120960 A1 | 5/2016 | McIvor et al. |

OTHER PUBLICATIONS

Devarajan et al. 2015 Book Chapter-Targeted Drug Delivery: Concepts and Design pp. 113-148, relevant 4 pages enclosed).*
Heinemann, DDT 1999;4:72-79.*
Wikipedia: Virus, 2018.*
Niemir et al. Hum Mole Genetics 2018.*
Serpi et al, Nucleoside Derived Antibiotics to Fight Microbial Drug Resistance: New Utilities for an Established Class of Drugs?, J. Med. Chern. 2016, 59, 10343-10382.*
Davison et al, A New Natural Product Analog of Blasticidin S Reveals Cellular Uptake Facilitated by the NorA Multidrug Transporter, Antimicrobial Agents and Chemotherapy, 2017, pp. 1-17.*
Orkin et al., UReport and Recommendations of the Panel to Assess the NIH Investment in Research on Gene Therapy, Issued By the U.S. National Institutes of Health, Bethesda, MD, Dec. 7, 1995.*
Fumoto etal, Targeted Gene Delivery: Importance of Administration Routes, Chapter 1, Intech, 2013, pp. 3-3.*
Baker et al., The Influence of Blood on In Vivo Adenovirus Bio-distribution and Transduction, Molecular Therapy, 2007, pp. 1410-1416.*
Varnavski et al., Evaluation of toxicity from high-dose systemic administration of recombinant adenovirus vector in vector-naive and pre-immunized mice, Gene Therapy (2005) 12, 427-436.*
Voigtlander et al., A Novel Adenoviral Hybrid-vector System Carrying a Plasmid Replicon for Safe and Efficient Cell and Gene Therapeutic Applications, Molecular Therapy-Nucleic Acids (2013), pp. 1-14.*
Bishop et al., "Molecular mechanisms of B-lymphocyte transformation by Epstein-Barr virus," Microbes and nfection, 4:853-857, 2002.
Carey et al., "Reprogramming of murine and human somatic cells using a single polycistronic vector," Proc. Natl. Acad. Sci. USA, 106:157-162, 2009.
Hettich et al. , "Genetic design of an optimized packaging cell line for gene vectors transducing human B cells," Gene Ther., 13(10):844-56, 2006.
Wendtner et al.,. "High level of transgene expression in primary chronic lymphocytic leukemia cells using helper-virus-free recombinant Epstein-Barr virus vectors," Exp. Hematol., 31(2):99-108, 2003.
Freitas et al., "Modified blasticidin S resistance gene (bsrm) as a selectable marker for construction of retroviral vectors," Journal of Biotechnology, 95 (2002) 57-62.
Magin-Lachmann et al., "Retrofitting BACs with G418 resistance, luciferase, and oriP and EBNA-1—new vectors for in vitro and in vivo delivery," BMC Biotechnology, 2003, 3:2.
Metz et al., "Bicistronic and Two-Gene Retroviral Vectors for Using MDR1 as a Selectable Marker and a Therapeutic Gene," Virology, 217, 230-241 (1996).
Ledley et al. , "Retroviral gene transfer into primary hepatocytes: Implications for genetic therapy of liver-specific functions," PNAS, vol. 84, pp. 5335-5339, Aug. 1987.
Ida et al., "Inducible Gene Expression by Retrovirus-Mediated Transfer of a Modified Tetracycline-Regulated System," Journal of Virology, Sep. 1996, p. 6054-6059.
Woo et al., "Therapeutic potential of adenovirus-mediated delivery of b-defensin 2 for experimental otitis media," Innate Immunity, 2015, vol. 21(2) 215-224.
Han et al., "An Efficient Vector System to Modify Cells Genetically," Plos One, Nov. 2011, vol. 6. Issue 11.
Ekhterae et al., "Retroviral Vector-Mediated Transfer of the Bacterial Neomycin Resistance Gene Into Fetal and Adult Sheep and Human Hematopoietic Progenitors In Vitro," Blood, vol. 75, No. 2 (Jan. 15, 1990): pp. 365-369.
Ben-Dor et al., "Lentiviral Vectors Harboring a Dual-Gene System Allow High and Homogeneous Transgene Expression in Selected Polyclonal Human Embryonic Stem Cells," Molecular Therapy, vol. 14, No. 2, Aug. 2006.
Harmoinen et al., "Orally Administered Targeted Recombinant Beta-Lactamase Prevents Ampicillin-Induced Selective Pressure on the Gut Microbiota: a Novel Approach to Reducing Antimicrobial Resistance," Antimicrobial Agents and Chemotherapy, Jan. 2004, p. 75-79.
Yin et al., "Overcoming multidrug resistance by co-delivery of Mdr-1 and survivin-targeting RNA with reduction-responsible cationic poly(b-amino esters)," Biomaterials, 33 (2012) 6495-6506.
Rein et al., "Combination of a MDR1-targeted replicative adenovirus and chemotherapy for the therapy of pretreated ovarian cancer," J Cancer Res Clin Oncol, (2012), 138:603-610.
Zaboikin et al., "Gene therapy with drug resistance genes," Cancer Gene Therapy, (2006) 13, 335-345.
Rein et al., "Treatment of chemotherapy resistant ovarian cancer with a MDR1 targeted oncolytic adenovirus," Gynecologic Oncology, 123(2011), 138-146.
Morizono et al., "Lentiviral vector retargeting to P-glycoprotein on metastatic melanoma through intravenous njection," Nature Medicine, vol. 11, No. 3, Mar. 2005.
Lee et al., "Retroviral Transfer of Human MDR1 Gene into Human T Lymphocytes," Methods In Enzymology, vol. 292.
Ramachandra et al., "Recombinant Vaccinia Virus Vectors for Functional Expression of P-Glycoprotein in Mammalian Cells," Methods In Enzymology, vol. 292.
Zhou et al., "Co-Expression of Human Adenosine Deaminase and Multidrug Resistance Using a Bicistronic Retroviral Vector," Human Gene Therapy, 9:287-293 (Feb. 10, 1998).
Podda et al., "Transfer and expression of the human multiple drug resistance gene into live mice," PNAS, vol. 89, op. 9676-9680, Oct. 1992.

(56) References Cited

OTHER PUBLICATIONS

Pastan et al., "A retrovirus carrying an MDRJ cDNA confers multidrug resistance and polarized expression of p. glycoprotein in MDCK cells," PNAS, vol. 85, pp. 4486-4490, Jun. 1988.
Xue et al., "Conditional Replication of a Recombinant Adenovirus Studied Using Neomycin as a Selective Marker," Journal of Biochemistry and Molecular Biology, vol. 36, No. 3, May 2003, pp. 275-281.
Chen et al., "A novel adenoviral vector carrying an all-in-one Tet-On system with an autoregulatory loop for tight, nducible transgene expression," BMC Biotechnology, (2015) 15:4.
Jiang et al., "Rapamycin Enhances Adenovirus-Mediated Cancer Imaging and Therapy in Pre-Immunized Murine Hosts," Plos One, Sep. 2013, vol. 8, Issue 9.
Sakurai et al., "Adenovirus serotype 35 vector-induced innate immune responses in dendritic cells derived from Arild-type and human CD46-transgenic mice: Comparison with a fiber-substituted Ad vector containing fiber proteins of Ad serotype 35," Journal of Controlled Release, 148 (2010) 212-218.
Lu et al., "Adaptive Seamless Design for An Efficacy Trial of ReplicationCompetent Adenovirus-mediated Suicide Gene Therapy and Radiation in Newly-diagnosed Prostate Cancer (ReCAP Trial)," Contemp Clin Trials, May 2011; 32(3): 453-460.
Lan Tran et al., "Prevention of Bleomycin-induced Pulmonary Fibrosis After Adenovirus-mediated Transfer of the Bacterial Bleomycin Resistance Gene," JCI, vol. 99, No. 4, Feb. 1997, 608-617.
Kasuya et al., "Passive Immunotherapy for Anthrax Toxin Mediated by an Adenovirus Expressing an Anti-Protective Antigen Single-Chain Antibody," Molecular Therapy, vol. 11, No. 2, Feb. 2005.
Smith-Arica et al., "Cell-Type-Specific and Regulatable Transgenesis in the Adult Brain: Adenovirus-Encoded Combined Transcriptional Targeting and Inducible Transgene Expression," Molecular Therapy, vol. 2, No. 6, Dec. 2000.
Reix et al., "Cytokine pattern in cystic fibrosis patients during antibiotic therapy and gene therapy using adenoviral vector," European Cytokine Network, 2002;13(3):324-30.
Steinwede et al., "Local delivery of Granulocyte/Macrophage Colony Stimulating Factor protects mice from lethal pneumococcal pneumonia," J Immunol Nov. 15, 2011; 187(10): 5346-5356.
Hu et al., "Development of an Adenovirus Vector with Tetracycline-regulatable Human Tumor Necrosis Factor a Sene Expression," Cancer Research 57 3339-3343. Aug. 15, 1997.
Stiefel et al., "Oral Administration of b-Lactamase Preserves Colonization Resistance of Piperacillin-Treated Mice," The Journal of Infectious Diseases, 2003; 188:1605-9.
Harmoinen et al., "Enzymic degradation of a P-lactam antibiotic, ampicillin, in the gut: a novel treatment modality," Journal of Antimicrobial Chemotherapy (2003) 51, 361-365.
Tarkkanen et al., "P1A Recombinant -Lactamase Prevents Emergence of Antimicrobial Resistance in Gut Microflora of Healthy Subjects during Intravenous Administration of Ampicillin," Antimicrobial Agents and Chemotherapy, Jun. 2009, p. 2455-2462.
Crowther et al., "Antibiotic therapy and Clostridium difficile infection—primum non nocere—first do no harm," Infection and Drug Resistance 2015:8 333-337.
Van Doren et al., "Infection of Eucaryotic Cells by Helper-Independent Recombinant Adenoviruses: Early Region 1 Is Not Obligatory for Integration of Viral DNA," Journal of Virology, May 1984, p. 606-614.
Massie et al., "Inducible Overexpression of a Toxic Protein by an Adenovirus Vector with a Tetracycline-Regulatable Expression Cassette," Journal of Virology, Mar. 1998, p. 2289-2296.
Ghersa et al., "Highly controlled gene expression using combinations of a tissue-specific promoter, recombinant adenovirus and a tetracycline-regulatable transcription factor," Gene Therapy, (1998) 5, 1213-1220.
Dentlivre et al., "Autoregulatory lentiviral vectors allow multiple cycles of doxycycline-inducible gene expression n human hematopoietic cells in vivo," Gene Therapy, (2010) 17, 14-25.
Nightingale et al., "Transient Gene Expression by Nonintegrating Lentiviral Vectors," Molecular Therapy, vol. 13, No. 6, Jun. 2006.
Bouard et al., "Viral vectors: from virology to transgene expression," British Journal of Pharmacology, (2009), 157, 153-165.
Flick and Pettersson, "Reverse Genetics System for Uukuniemi Virus (Bunyaviridae): RNA Polymerase l-Catalyzed Expression of Chimeric Viral RNAs," Journal of Virology, Feb. 2001, p. 1643-1655.
Li et al., "Engineering influenza viral vectors," Bioengineered, 4:1, 9-14; Jan./Feb. 2013.
Osakada and Callaway, "Design and generation of recombinant rabies virus vectors," Nat Protoc. Aug. 3, 2013(8): 1583-1601.
Cronin et al., "Altering the Tropism of Lentiviral Vectors through Pseudotyping," Curr Gene Ther., Aug. 2005; 5(4): 387-398.
Lukashchuk et al., "AAV9-mediated central nervous system-targeted gene delivery via cisterna magna route in mice," Molecular Therapy—Methods & Clinical Development (2016) 3, 15055.
Danthinne, X., and Imperiale, J., "Production of first generation adenovirus vectors: a review," Nature, 7(20) 1707-1714, 2000.
Raboulle, C., "Pathways of Unconventional Protein Secretion," Trends in Cell Biology, 1305, 2016 (11 pages).
SCITABLE (a division of the company that publishes the journal Nature), definition: "promoter", http://www.nature.com/scitable/definition/promoter-259.
Berg, J.M., et al., "Section 8.4, The Michaelis-Menten Model Accounts for the Kinetic Properties of Many Enzymes," Biochemistry, 5th Edition, NCBI Bookshelf, National Library of Medicine, National Institutes of Health, WH Freeman, New York, 2002.
Silva, M.T., "Classical labeling of bacterial pathogens according to their lifestyle in the host: inconsistencies and alternatives," Frontiers in Microbiology, 3:71, Feb. 29, 2012.
Cordon-Cardo, C., et al., "Expression of the Multidrug Resistance Gene Product (P-Glycoprotein) in Human Normal and Tumor Tissues," Journal of Histochemistry and Cytochemistry, vol. 38, No. 9, pp. 1277-1287, 1990.
Izumi, et al., "Blasticidin S-Resistance Gene (bsr): A Novel Selectable Marker for Mammalian Cells," Experimental Ceil Research, 197, 229-233 (1991).
MeSH Supplementary, "blasticidin S," revised Nov. 5, 2012, National Institutes of Health, Health & Human Services, USA.gov.
Ding, H., et al., "Tranformation of Sexually Transmitted Infection-Causing Serovars of Chlamydia trachomatis Using BLasticidin for Selection," PLoS ONE 8(11): e80534. doi:10,1371/journal.pone.0080534 (2013).
"Chlamydial infections," Centers for Disease Control and Prevention, www.cdc.gov/std/tg2015/chlamydia.htm , Jun. 4, 2015.
"Plague Fact Sheet," World Health Organization, http://www.who.int/mediacentre/factsheets/fs267/en/, Oct. 2017.
Urabe, M., et al., "A novel dicistronic AAV vector using a short IRES segment derived from hepatitis C virus genome," Gene, 200(1-2): 157-162; 1997.
Lukashchuk, V., et al., "AAV9-mediated central nervous system-targeted gene delivery via cistema magna route in nice," Nature, Official Journal of the American Society of Gene & Cell Therapy, Molecular Therapy—Methods and Clinical Development, 3(15055), DOI: 10.1038/mtm.2015.55, 2016.
De Backer, M.W ., et al., "An adeno-associated viral vector transduces the rat hypothalamus and amygdala more efficient than a lentiviral vector," BMC Neuroscience, 11(81), DOI: 10.1186/1471-2202/11/81, 2010.
Fink, M.P, etaL, "Treatment of Severe Pneumonia in Hospitalized Patients: Results of a Multicenter, Randomized, Double-Blind Trial Comparing Intravenous Ciprofloxacin with Imipenem-Cilastatin," Antimicrobial Agents and Ghemotherapy, 38(3): 547-557, 1994.
Gin, J.Y., et al., "Systematic comparison of constitutive promoters and the doxycycline-inducible promoter," PLoS One, 5(5); e10611, DOI: 10.1371/joumal.pone.0010611, 2010.
Niimi, K., et al., "Overexpression of Candida albicons CDR1, CDR2, or MDR1 does not produce significant changes in echinocandin susceptibility," Antimicrobial Agents And Chemotherapy, 50(4): 1148-1155, 2006.
Gowman, A.F., et al., "Selection for Mefloquine Resistance in Plasmodium falciparum is Linked to Amplification of the ofmdr1

(56) References Cited

OTHER PUBLICATIONS

Gene and Cross-Resistance to Halofantrine and Quinine," Proc. Nat. Acad. Sci. USA, 91(3):1143-1145, 1994.
Garcia-Echauri, S.A., et al., "TETX: a novel nuclear selection marker for Chlamydomonas reinhardtii Yansformation," Plant Methods, 11:27, DOI: 10.1186/s13007-015-0064-8, 2015.
Lan, K.H., et al., "Tumor-Specific Gene Expression in Carcinoembryonic Antigen-Producing Gastric Cancer Cells Jsing Adenovirus Vectors," Gastroenterology, 111(5):1241-1251, 1996.
Gao, J.Q., et al., "Cotransduction of CCL27 gene can improve the efficacy and safety of IL-12 gene therapy for Dancer," Gene Therapy, 14(6):491-502, 2007.
Kugler, S., et al., "Human synapsin 1 gene promoter confers highly neuron-specific long-term transgene expression Yam an adenoviral vector in the adult rat brain depending on the transduced area," Gene Therapy, 10(4):334-347, 2003.
Salva, M.Z., et al., "Design of Tissue-specific Regulatory Cassettes for High-level rAAV-mediated Expression in Skeletal and Cardiac Muscle," Molecular Therapy, 15(2)1320-329, 2007.
Polo, J.M., et al., "Stable alphavirus packaging cell lines for Sindbis virusand Semliki Forest virus-derived vectors," Proc. Nat. Acad. Sci. USA, 96(8):4598-1603, 1999.
Pushko, P., et al., "Replicon-Helper Systems from Attenuated Venezuelan Equine Encephalitis Virus: Expression of Heterologous Genes in Vitro and Immunization against Heterologous Pathogens in Vivo," Virology, 239(2)1389-401, 1997.
Patel, M., et al., "High efficiency gene transfer to airways of mice using influenza hemagglutinin pseudotyped entiviral vectors," Journal of Gene Medicine, 15(1)151-62, DOI: 10.1002/jgm.2695, 2013.
Bozdogan, B., et al., "Effects of Genes Encoding Resistance to Streptogramins A and Bon the Activity of Quinupristin-Dalfopristin against Enterococcus faecium," Antimicrobial Agents and Chemotherapy, 43(11):2720-2725, 1999.
Lu, H. et al., "Enhanced Gene Expression in Breast Cancer Cells in Vitro and Tumors in Vivo," Molecular Therapy, 6(6):783-792, 2002.
Rodriguez-Fonseca, et al., "Fine Structure of the Peptidyl Transferase Centre on23 S-like rRNAs Deduced from Chemical Probing of Antibiotic-Ribosome Complexes," J. Mol. Biol. 247:224 235,1995.
Jima, et al., "Successful Gene Therapy via Intraarticular Injection of Adenovirus Vector Containing CTLA4lgG in a Murine Model of Type II Collagen-Induced Arthritis," Human Gene Therapy, 12:1063-1077, Jun. 10, 2001.
Hioki, et al., "High-level transgene expression in neurons by lentivirus with Tet-Off system," Neuroscience Research 33:149-154, 2009.
Sharma, et al., "Adenovirus receptors and their implications in gene delivery," Virus Research 143:184-194, 2009.
Boye, et al., "Functional and Behavioral Restoration of Vision by Gene Therapy in the Guanylate Cyclase-1 (GC1) Knockout Mouse," PLoS ONE 5(6): e11306 doi:10.1371/journal.pone 0011306, 2010, pp. 1-13.
European Medicines Agency (EMA), Assessment Report, Glybera, EMA/CHMP/882900/2011, Jul. 19, 2011. pp. 1-147.
Regulation (EC) No. 1394/2007 Of the European Parliament and of the Council, Nov. 13, 2007. p. 1-17.
Boning, "Gene therapy enters the pharma market: the short story of a long journey," EMBO Mol Med 5:1-3, 2012.
Akil, et al., "Restoration of Hearing in the VGLUT3 Knockout Mouse Using Virally-Mediated Gene Therapy," Neuron, 75(2):283-293, NIH Public Access, doi:10 1016/j neuron.2012 05.019, Jul. 26, 2012.
Wold & Toth, "Adenovirus Vectors for Gene Therapy, Vaccination and Cancer Gene Therapy," Curr Gene Therapy 13(6):421-433, Dec. 2013.
European Medicines Agency (EMA), Assessment Report, Strimvelis, EMA/CHMP/272303/2016, Apr. 1, 2016. pp. 1-195.
European Medicines Agency (EMA), Press Release, "New gene therapy for the treatment of children with ultra-rare immune disorder recommended for approval," EMA/CHMP/230486/2016, Apr. 1, 2016, pp. 1-3.
Yue, et al., "Survivin-TGFB3-TIMP1 Gene Therapy Via Lentivirus Vector Slows the Course of Intervertebral Disc Degeneration in an In Vivo Rabbit Model," SPINE vol. 41, No. 11, pp. 926-934, 2016.
Misato, T., "Blasticidin S." In: Gottlieb D., Shaw P.D. (eds) Antibiotics. Springer, Berlin, Heidelberg, 1967, pp. 434-435.

\* cited by examiner

METHOD TO KILL PATHOGENIC MICROBES IN A PATIENT

BACKGROUND

Each year, millions of people die as a result of microbial infection. In particular, bacteria, parasites, and fungi present a major health threat to humans and other mammals. Typically, microbial infection is combated with the administration of antimicrobial medications. For example, a bacterial infection may be treated with antibiotic medication, a fungal infection may be treated with antifungal medication, and a parasite may be treated with antiparasitic medication. The goal of the antimicrobial treatment is to kill a large number of the microbes without excessively harming the patient, whether the patient is a human or another mammal. However, current treatment by many antimicrobial medications may results in adverse events, which are more commonly known as side effects. For example, administration of the antimicrobial blasticidin S may cause death in humans, and administration of the antibacterial agents ciprofloxacin and levofloxacin (a chiral fluorinated carboxyquinolone) increases the risk of tendon rupture in humans.

Furthermore, the development of resistance to antimicrobials in microbes has become a rising global health threat. For example, methicillin-resistant *Staphylococcus aureus* (MRSA) causes at least 80,000 invasive infections each year in the United States, which result in over 11,000 deaths. Antimicrobial resistance can be conferred through the expression of an antimicrobial resistance gene. The gene typically codes for an enzyme, which can interact with the antimicrobial medication or its target in a way that neutralizes the antimicrobial's toxicity to the microbe. For example, many microbes express the gene neo, which codes for aminoglycoside 3'-phosphotransferase, which phosphorylates neomycin's 3' hydroxyl group, thereby preventing neomycin from disrupting protein synthesis.

Hence, there is a need in the art for improved methods to kill microbes in a patient.

DETAILED DESCRIPTION OF EXAMPLE EMBODIMENTS

Figure 1:
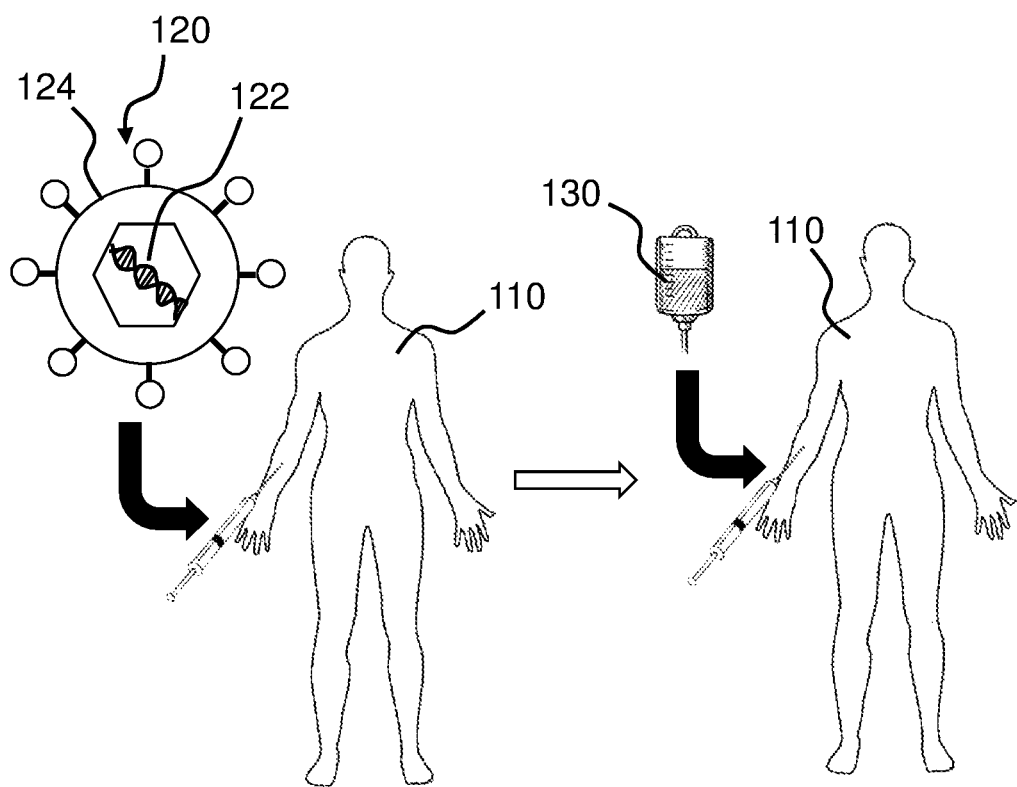
FIG. 1 schematically depicts a macroscopic view of an exemplary embodiment of the present invention.

Antimicrobial medications are administered to patients for the purpose of inhibiting the growth of, or killing, pathogenic microbes. In addition to inhibiting the growth of or killing pathogenic microbes, antimicrobial medications can cause adverse events in the patient after administration. Antimicrobial medications may include, for example, antibacterial, antifungal, and anti-parasitic agents.

Antibiotic agents may be used as an antimicrobial medication, and may include (without limitation) penicillins, penicillin combinations, cephalosporins, tetracyclines, beta-lactam antibiotics, carbacephems, glycopeptides, aminoglycosides, ansamycins, macrolides, monobactams, nitrofurans, sulfonamides, lincosamides, lipopeptides, polypeptides, quinolones, drugs against mycobacteria, oxazolidinones, chloramphenicol, fosfomycin, metronidazole, mupirocin, platensimycin, quinupristin/dalfopristin, thiamphenicol, tigecycline, tinidazole and trimethoprim and mixtures thereof.

Antibiotic agents may range in toxicity from death to no effect on the patient. Exemplary antibiotic agents include G418 (geneticin), mycophenolic acid, puromycin, blasticidin S, cefsulodin, cycloheximide, cephalothin, dihydrostreptomycin, zeocin, penicillin, penicillin G, penicillin V, amoxicillin, ampicillin, azlocillin, carbenicillin, cloxacillin, dicloxacillin, flucloxacillin, mezlocillin, methicillin, nafcillin, oxacillin, temocillin, ticarcillin, amoxicillin/clavulanate, ampicillin/sulbactam, piperacillin/tazobactam, ticarcillin/clavulanate, demeclocycline, doxycycline, minocycline, oxytetracycline, tetracycline, cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinome, ceftobiprole, ceftaroline, cefaloram, cefaparole, cefcanel, cefedrolor, cefempidone, cefetrizole, cefivitril, cefmepidium, cefoxazole, cefrotil, cefsumide, ceftioxide, cefuracetime, ertapenem, doripenem, imipenem, imipenem/cilastatin, meropenem, panipenem/betamipron, biapenem, razupenem, tebipenem, teicoplanin, vancomycin, ramoplanin, telavancin, streptomycin, gentamicin, kanamycin, neomycin, netilmicin, tobramycin, spectinomycin, paromomycin, framycetin, ribostamycin, amikacin, arbekacin, bekanamycin, dibekacin, rhodostreptomycin, apramycin, hygromycin B, sisomicin, isepamicin, verdamicin, astromicin, rifaximin, azithromycin, clarithromycin, dirithromycin, erythromycin, roxithromycin, carbomycin, josamycin, kitasamycin, midecamycin, oleandomycin, solithromycin, spiramycin, troleandomycin, tylosin, cethromycin, aztreonam, furazolidone, nitrofurantoin, nifuroxazide, sulfamethoxazole, sulfisomidine, sulfadiazine, sulfamethizole, sulfanilamide, sulfisoxazole, trimethoprim-sulfamethoxazole, sulfacetamide, clindamycin, lincomycin, daptomycin, bacitracin, colistin, polymyxin B, moxifloxacin, ciprofloxacin, levofloxacin, nalidixic acid, oxolinic acid, piromidic acid, pipemidic acid, rosoxacin, enoxacin, lomefloxacin, nadifloxacin, norfloxacin, ofloxacin, pefloxacin, rufloxacin, balofloxacin, grepafloxacin, pazufloxacin, sparfloxacin, tosufloxacin, clinafloxacin, gatifloxacin, gemifloxacin, sitafloxacin, trovafloxacin, prulifloxacin, clofazimine, dapsone, capreomycin, cycloserine, ethambutol, ethionamide, isoniazid, pyrazinamide, rifampicin, rifabutin, rifapentine, streptomycin, linezolid, posizolid, radezolid, torezolid, chloramphenicol, fosfomycin, metronidazole, platensimycin, quinupristin/dalfopristin, thiamphenicol, tigecycline, tinidazole, trimethoprim and combinations thereof.

Antifungal agents may belong to the class azoles, polyenes, echinocandins, or flucytosine, for example. Exemplary antifungal agents include clotrimazole, econazole, isavuconazonium sulfate, itraconazole, fluconazole, ketoconazole, miconazole, posaconazole, voriconazole, amphotericin B, natamycin, nystatin, anidulafungin, caspofungin, micafungin, griseofulvin, flucytosine, terbinafine, cycloheximide, and combinations thereof.

Antiparasitic agents may include metronidazole, iodoquinol, paromomycin, sulphadiazine, pyrimethamine, doxycycline, mefloquin, malarone, coartem, plaquenil, artemether/lumefantrine, and chloroquine, for example. Antimicrobial agents may also be used for prophylaxis. For example, antimicrobial agents used for prophylaxis may include atovaquone/proguanil, chloroquine, doxycycline, mefloquine, primaquine, cephazolin, vancomycin, clindamycin, metronidazole, ampicillin, and ertapenam.

Two or more antimicrobial agents may also be used in combination with each other in an antimicrobial medication. For example, clindamycin may be used with gentamicin, vancomycin may be used with quinolone, and pyrimethamine may be used with sulfadoxine.

Antimicrobial resistance genes, when expressed, may confer cellular resistance to one or more antimicrobial agents in various ways. For example, an efflux pump may pump the antimicrobial agent out of the cell, thus preventing the agent from reaching its target or reacting within the cell. Alternatively, the antimicrobial resistance gene may code for a protein that catalyzes a reaction that renders the antimicrobial agent unable to interact with its target. Alternatively, the antimicrobial resistance gene may code for an enzyme that modifies the target of the antimicrobial agent. For example, the antimicrobial resistance gene may reduce the binding affinity of the antimicrobial agent's target to the antimicrobial agent, so that the antimicrobial agent cannot bind well enough to induce microbial death.

Antimicrobial resistance genes may also be classified by the primary antimicrobial agent to which they confer resistance (e.g. an antibiotic resistance gene, an antifungal resistance gene, an antiparasitic resistance gene, or a gene that confers resistance to multiple antimicrobial agents). For example, the antimicrobial resistance gene $bla_{CMY-25}$ specifically confers resistance to β-lactam antibiotics, whereas the antimicrobial resistance gene MRP1 may confer resistance to a wide range of xenobiotic agents including antibiotic, antifungal, and antiparasitic agents.

Many different genes, when expressed, may confer resistance to one or more antibacterial agents. Some such genes that are derived from bacteria include: neo, sh ble, hph, bsr, pac, aac(3)-Iia, aac(6')-Ie, aac(2')-Ia, ant(2'')-Ic, ant(4')-Iia, ant(6)-Ia, aph(3')-Ib, aph(3')-Via, aph(6)-Ia, $bla_{CMY-1}$, $bla_{CMY-25}$, $bla_{CMY-50}$, $bla_{TEM-1}$, $bla_{TEM-3}$, $bla_{TEM-30}$, $bla_{TEM-50}$, $bla_{SHV-1}$, $bla_{SHV-2}$, $bla_{SHV-10}$, $bla_{CTX-M-1}$, $bla_{PER-1}$, $bla_{VEB-1}$, $bla_{GES-2}$, $bla_{KPC-2}$, $bla_{SME-1}$, $bla_{OXA-1}$, $bla_{OXA-11}$, $bla_{OXA-23}$, $bla_{IMP-1}$, $bla_{VIM-1}$, $bla_{IND-1}$, $bla_{AMPC}$, ermA, ermB, carA, msrA/msrB, vgaA, vgaB, tlrC, mefA, mefE, lmrA, ereA, ereB, vgb, lnuA, linG, vatA, vatD, mphA, efrAB, emeA, lsa, emrD, mdfA, emrB, acrA, acrB, tolC, acrF, tehA, mexA, mexB, oprM, otrB, tetA, tetE, tetH, tetK, tetL, tcr3, otrA, tetW, tetX, norA, and mdeA.

Many different genes, when expressed, may confer resistance to one or more antifungal agents. Some of these genes found in fungi include: CDR1, CDR2, CDR3, CDR4, CDR5, Pdr1, Pdr5, MDRA, Yor1, AtrA, AtrB, AtrF, AtrL, Flr1, CaMDR1, and Snq2.

Several parasites have genes that may confer resistance to antimicrobial agents. Some such genes that code for antiparasitic agent resistance include: Plasmodium falciparum crt1(pfcrt1), pfmdr1, pfmdr1-86N, pfmdr1-K76, pfmdr1-76T, pfnhe1, Plasmodium vivax mdr1 (pvmdr1), pvmdr1-Y976F, Plasmodium oxidative stress complex, TCP-1 ring complex, cyclophilin19B, dolichyl-phosphate-mannose protein mannosyltransferase, endoplasmic reticulum-resident calcium binding protein, protein disulfide isomerase, Toxoplasma gondii crt (tgcrt), tgABC.B1, tgABC.B2, tgABC.C1, and *Trichomonas vagninalis* pgp1 (tvpgp1).

Other animals such as humans also have genes that may provide resistance against antimicrobial agents, such as: ABCG2, MRP1, MRP2, MRP3, MRP4, MRP5, MRP6, PGP, OAT1, OAT2, OAT3, OCT1, VMAT1, and MTP.

A promoter is a sequence of nucleic acids located upstream of a gene that helps regulate the expression of the downstream gene(s). The promoter may regulate gene expression by binding to transcription factors, which in turn recruit RNA polymerase. RNA polymerase may then transcribe the gene into mRNA, which may subsequently translocate to a ribosome where it is translated into a protein.

Certain promoters may drive the recombinant gene expression with different strengths. For example, a weak promoter may induce a lower level of gene expression than a strong promoter. The expression pattern of the promoter may be determined by the transcription factors to which it binds. Some promoters bind transcription factors that are broadly active. Ubiquitous promoters are strongly active in a wide range of cell types and tissues, and so may induce expression of their gene in a wide range of cell types and/or organisms.

Certain embodiments of the present invention may use one or more ubiquitous promoters, for example: human β-actin promoter, EF-1 promoter, EGR-1 promoter, eIF4A1 promoter, CMV promoter, RSV promoter, FerH promoter, FerL promoter, GAPDH promoter, GRP78 promoter, GRP94 promoter, HSP70 promoter, β-Kin promoter, PGK-1 promoter, ROSA promoter, ubiquitin B promoter, TEF1 promoter, H1 promoter, and U6 promoter.

In contrast to ubiquitous promoters, tissue-specific promoters primarily bind their transcription factors in a certain cell or tissue type. Genes downstream of a tissue-specific promoter are expressed primarily when they are located in a cell of their promoter's specific tissue type. Certain embodiments of the present invention may use a tissue-specific promoter, for example: B29 promoter, CD14 promoter, CD43 promoter, CD45 promoter, desmin promoter, elastase-1 promoter, endoglin promoter, fibronectin promoter, Flt-1 promoter, GFAP promoter, GPIIb promoter, ICAM-2 promoter, mIFNβ promoter, Mb promoter, Nphsl promoter, OG-2 promoter, SP-C promoter, SYN-1 promoter, WASP promoter, and CaMKIIa promoter.

An inducible promoter does not respond to endogenous signals, but instead responds to exogenous stimuli, which may be artificially controlled. Upon administration of the inducible promoter's stimuli, the inducible promoter is turned on, and allows expression of its downstream gene. Certain embodiments of the present invention may use an inducible promoter, for example: the streptogramin regulated expression system (PIP), the tetracycline on expression system (TetOn), the macrolide regulated expression system (E.REX), the rapamycin gene regulation system, the RU486 gene regulation system, and the HRE gene regulation system.

Synthetic promoters may be made by bringing together different primary elements of a promoter region from various origins. Hence, a synthetic promoter may be ubiquitous, tissue-specific, or inducible. Certain embodiments of the present invention may use a synthetic promoter, for example: CAG promoter, βAct/RU5' promoter, EF1/RU5' promoter, SV40/hFerH/mEF1 promoter, SV40/bAlb promoter, SV40/hAlb promoter, SV40/CD43 promoter, SV40/CD45 promoter, and NSE/RU5' promoter.

In certain embodiments of the present invention, a viral vector is used to deliver an antimicrobial resistance gene to eukaryotic cells of a patient. The viral vector preferably encodes an antimicrobial resistance gene, a promoter, as well as the necessary viral genes for packaging and to induce expression of the antimicrobial resistance gene in the transduced cell. For safety, the viral vector is preferably replication defective, meaning that it will not have the ability to replicate upon transfecting a cell. For example, a wild type lentivirus' genome includes the GAG, POL, REV, TAT, ENV, VIF, VPR, VPU, TAT, and NEF genes. However, a replication deficient lentivirus vector's genome may include the GAG, POL, REV, and TAT genes, and a recombinant promoter and antimicrobial resistance gene, but lack the ENV, VIF, VPR, VPU, TAT, and NEF genes. In another example, an adenovirus vector genome may include inverted terminal repeats (ITRs), promoters, genes E2, E4, L1, L2, L3, L4, and L5, and a recombinant promoter and antimicrobial resistance gene, but may lack the E1 and E3 genes necessary for replication.

In certain embodiments of the present invention, viruses used as vectors may be drawn from the adenoviridae, arenaviridae, bunyaviridae, flaviviridae, hepadnaviridae, herpesviridae, orthomyxoviridae, papovaviridae, paramyxoviridae, parvoviridae, picornaviridae, poxviridae, reoviridae, retroviridae, rhabdoviridae, and togaviridae families. For example, in certain embodiments of the present invention, viruses used as vectors may include: human adenovirus serotype 5 (HAdV-5), HAdV-11, HAdV-35, LCMV WE, LCMV Armstrong, Uukuniemi virus, Bunyamwera virus, Kunjin virus, tick-borne encephalitis virus, hepatitis B virus, HSV-1, HSV-2, HPV, BPV, influenza A virus, influenza B virus, influenza C virus, adeno-associated virus serotype 1 (AAV1), AAV6, AAV9, measles virus, rhinovirus, poliovirus, vaccinia virus, modified vaccinia ankara virus, NYVAC, ALVAC, TROVAC, reovirus (including mutants, particularly with mutations in the σ1 and λ2 viral genes), BIV, FIV, HIV-1, HIV-2, HTLV-1, HTLV-2, HTLV-5, SIV, visna virus, rabies virus, VSV, Ross River virus, Sindbis virus, Semliki virus, and Venezuelan equine encephalitis virus.

In certain embodiments of the present invention, the viral vector may be modified to have a different tropism than normal. That is, it may be modified to transfect a broader or narrower set of host cells than the wild type vector. The viral vector with modified tropism may primarily target the delivery of the antimicrobial resistance genes to one or more specific tissue or cell types. For example, a lentivirus may be pseudotyped to express a different surface protein than the wild type form. Modifying a lentiviral vector's pseudotype to be vesicular stomatitis virus (VSV) may give it a broader tropism. However, lentiviral vectors may be given other pseudotypes such as rabies virus, LCMV, ross river virus, Marburg virus, avian leukosis virus, jaagsiekte sheep retrovirus, gibbon ape leukemia virus, HTLV-1, human foamy virus, maedi-visna virus, SARS-CoV, sendai virus, hepatitis C virus, influenza virus, and *Autographa californica* multiple nucleopolyhedro virus. As described in certain examples herein, some embodiments of the present invention may include modifying the tropism of the viral vector to more effectively target certain cell types or reduce or prevent transduction of other cell types.

Some antimicrobial agents are so toxic that they kill both microbes, and eukaryotic cells. Therefore, in vitro, certain eukaryotic cells may be deliberately and selectively killed by application of a toxic antimicrobial agent, after other cells in the laboratory culture have been transfected with foreign nucleic acid containing a gene of interest and an antimicrobial resistance gene. That is, in laboratory cell cultures, one may use toxic antimicrobials to select for eukaryotic cells that have been transfected with the gene of interest, by killing the eukaryotic cells that have not been transfected.

For example, the antimicrobial puromycin kills both eukaryotic and prokaryotic cells by inhibiting protein synthesis. However, eukaryotic or prokaryotic cells that have been transfected with a gene of interest and the pac gene, which codes for puromycin N-acetyl-transferase, are resistant to puromycin, and therefore will survive puromycin treatment. Such treatment may be used to create a laboratory cell culture that is homogeneous (in that every cell expresses the gene of interest).

However, selecting and killing eukaryotic cells in vitro is not the same as protecting eukaryotic cells while killing microbes in vivo. Several embodiments of the present invention are directed to the latter objective.

FIG. 1 schematically depicts a macroscopic view of an exemplary embodiment of the present invention. A patient 110 is administered a recombinant viral vector 120, which contains in its genome one or more antimicrobial resistance genes 122. Viruses may be enveloped or non-enveloped. Viruses that are enveloped have a membrane surrounding them, which primarily consists of phospholipids and proteins. Meanwhile, viruses that are non-enveloped do not have a membrane surrounding them; their outermost surface is the capsid, which may be made of protein. Retroviruses and togaviruses are examples of enveloped viruses, whereas adenoviruses and adeno-associated viruses are examples of non-enveloped viruses. The viral vector 120 shown in FIG. 1 is depicted as having a viral envelope 124, however the viral vector 120 used in several embodiments of the present invention may alternatively be non-enveloped.

In the embodiment of FIG. 1, the viral vector 120 preferably transfects only the patient's eukaryotic cells, so that pathogenic microbes will not be transduced with the antimicrobial resistance gene 122. The viral vector 120 could be specific for all of the patient's eukaryotic cells or certain tissues or cell types within the patient 110. For example, the viral vector 120 may target all of the patient's eukaryotic cells, or may target neural tissue, cardiac tissue, skeletal tissue, CD4 T cells, or B cells. Multiple viral vectors may also be administered. For example, the viral vector 120 may transduces all of the patient's eukaryotic cells, and could be administered before, at the same time, or after one or more other vectors that infect a certain tissue or cell type in the patient 110.

In this way, some eukaryotic cells within all tissues and cell types may be transduced with the antimicrobial resistance gene 122, and a higher proportion of eukaryotic cells may be transduced within a certain cell type or tissue. For example, one could administer a lentivirus vector with a VSV-G pseudotype to confer antimicrobial resistance in every type of the patient's eukaryotic cells, and an AAV1 vector to confer enhanced antimicrobial resistance to skeletal muscle, cardiac muscle, and central nervous system tissue in particular.

As shown in FIG. 1, the patient 110 is also administered an antimicrobial medication 130, which otherwise may be toxic to the patient 110 or have undesirable side effects on the patient 110 (if the viral vector 120 had not been administered).

Figure 2:
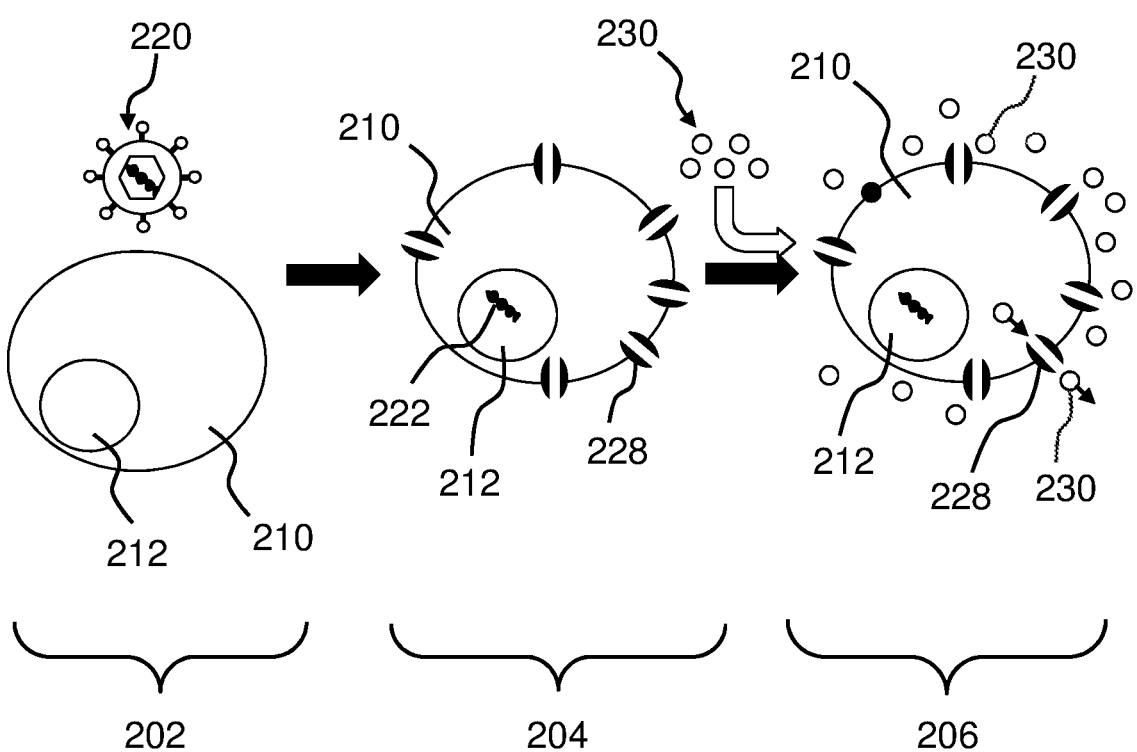
FIG. 2 schematically depicts a microscopic view of an exemplary embodiment of the present invention.

FIG. 2 schematically depicts a microscopic view of an exemplary embodiment of the present invention. In step 202, upon administration to the patient, a viral vector 220 containing a recombinant promoter and antimicrobial resistance gene will transfect the patient's eukaryotic cell 210 in vivo. The nucleic acid 222, which in this embodiment codes for an efflux pump and promoter, will then translocate to the nucleus 212 of the patient's eukaryotic cell 210 and will be converted into expressible double stranded DNA (dsDNA). However, the promoter and antimicrobial resistance gene that codes for an efflux pump may not be converted into dsDNA, if they are coming from a vector whose genome is dsDNA.

In step 204 of the embodiment of FIG. 2, the antimicrobial resistance gene in the transduced nucleic acid 222 that codes for an efflux pump is transcribed and translated, resulting in antimicrobial resistance efflux pumps 228 being expressed on the surface of the patient's eukaryotic cell 210.

In step 206 of the embodiment of FIG. 2, an antimicrobial agent 230 is administered to the patient. The antimicrobial agent 230 (e.g. administered to combat a microbial infection or for prophylaxis) may be administered before, at the same time as, or after the administration of the viral vector 220. In the embodiment of FIG. 2, the antimicrobial resistance efflux pump 228 will pump the antimicrobial agent 230 out of the patient's eukaryotic cell 210, preventing it from interacting with internal components of the patient's eukaryotic cell 210, and potentially increasing the extracellular concentration of the antimicrobial agent 230. In certain embodiments, this may decrease adverse side effects of the antimicrobial agent 230 to the patient, while maintaining or improving the efficacy of the antimicrobial agent 230 in destroying pathogenic microbes in vivo. In certain embodiments, this may enable the use of an otherwise toxic antimicrobial agent to be safely administered to a patient.

Example 1—Whole Organism Targeting Vector, and Approved Antibiotic Medication

Certain embodiments of the present invention allow for improved treatment of extracellular microbial infections (e.g. anthrax) with currently approved antimicrobials. In Example 1, a second-generation HAdV-35 adenovirus vector, containing the human PGP gene downstream of a human EF-1 promoter, is administered to the patient. Since PGP codes for a multidrug efflux pump, any antibiotic that is exported by the pump may be used, including quinolones like ciprofloxacin, macrolides like erythromycin and clarithromycin, and β-lactams like dicloxacillin, and tetracyclines like doxycycline. Example 1 may allow for flexibility in fighting anthrax, as treatment with many types of antibiotics may be enhanced by expression of the recombinant PGP gene. Ciprofloxacin is an antibiotic that may combat anthrax infection, and so is used in Example 1. However, another antibiotic like levofloxacin or doxycycline may be used, with appropriate changes in the timing, frequency, and/or dosage of either the adenovirus vector or the antibiotic.

Between $10^{11}$ to $10^{14}$ adenovirus vectors may be administered depending on various factors, which could include the weight, age, sex, genetic makeup, and other medications of the patient. The antibiotic may be administered at the amount and frequency that is in accordance with current medical practices to treat anthrax infection. Alternatively, the method of Example 1 advantageously may allow the antibiotic to be administered at a higher dose or frequency due to the increased resistance of the patient to ciprofloxacin. For example, in systemic anthrax infection in an adult, 400 mg ciprofloxacin initially may be administered intravenously every 12 hours. However, after administration of the HAdV-35 vector containing PGP, the dose may be increased to 600 mg every 12 hours or 400 mg every 8 hours.

According to the method of Example 1, the recombinant adenovirus vector may be administered intravenously to the patient before, at the same time as, or after ciprofloxacin. The recombinant vector may be administered between one month before and one day after ciprofloxacin depending on the clinical needs of the patient. The administered HAdV-35 vector will transduce the patient's eukaryotic cells, thus inducing expression of PGP. PGP serves to pump the ciprofloxacin out of the patient's cells (e.g. as shown in FIG. 2) and into the extracellular space where anthrax resides.

The method of Example 1 may increase the effective concentration of ciprofloxacin to which anthrax is exposed, which improves bacterial killing, and may also reduce the incidence and severity of ciprofloxacin's side effects, like fluoroquinolone-induced tendinopathy, that arise from interactions with ciprofloxacin inside the patient's cells.

Example 2—Whole Organism Targeting Vector, and Approved Antifungal Medication

The method of Example 2 shows how certain embodiments of the present invention may improve the treatment of extracellular fungal infections, like *Aspergillus fumigatus*. In Example 2, an AAV1 vector containing the CDR1 antifungal resistance gene downstream of the synthetic CAG promoter is administered to the patient. For example, between $10^{11}$ to $10^{14}$ adeno-associated virus vectors may be administered depending on various factors, which could include the weight, age, sex, genetic makeup, and other medications of the patient.

According to the method of Example 2, the antifungal medication voriconazole may be administered to the patient at a frequency and dosage that is in accordance with the current medical guidelines to treat *A. fumigatus* infection. The recombinant AAV1 vector may be administered intravenously to the patient any time before, to one day after voriconazole, depending on the clinical needs of the patient.

In Example 2, the administered recombinant AAV1 vector will transduce the patient's eukaryotic cells, thus inducing expression of CDR1. CDR1 will pump the ciprofloxacin out of the cells (e.g. as shown in FIG. 2) and into the extracellular space where *A. fumigatus* resides. Hence, the method of Example 2 may increases the effective concentration of voriconazole to which *Aspergillus* is exposed, which enhances fungal killing, and may also reduce the incidence and severity of voriconazole's adverse effects, like visual disturbances and hallucinations.

Example 3—Specific Tissue/Cell Targeting Vector, and Antiparasitic Medication for Prophylaxis or to Treat Infection Certain embodiments of the present invention allow for improved treatment of tissue-restricted intracellular microbial infections (e.g. malaria) with antimicrobial medications. For example, the method of Example 3 may increase the efficacy, and reduce the side effects of antimalarial prophylactic medication or medication to treat malaria infection.

Upon entering a host, malaria sporozoites will travel to the liver, where they enter liver cells and mature into schizonts. The schizonts then rupture the liver cell releasing merozoites. The merozoites then infect red blood cells where they differentiate into trophozoites. Finally, the trophozoites differentiate into gametocytes, which are ingested by an Anopheles mosquito during a blood meal, leading to further infection down the line. However, it is believed that malaria does not infect cells belonging to the central nervous system (CNS).

The antimicrobial medication mefloquine may be administered to the patient to treat malaria. However, administration of mefloquine may cause adverse neuropsychiatric effects, including anxiety, paranoia, depression, hallucinations, psychosis, dizziness or vertigo, tinnitus, loss of balance, suicidal ideation, and/or suicide.

According to Example 3, a self-complementary adeno-associated virus serotype 9 vector (scAAV9), with Hb9 promoter enhancer elements, and synapsin 1 (SYN1) promoter, that is upstream of pfmdr1, may be administered to the patient. This vector is neurotropic, and has promoter and enhancer elements that restrict expression to CNS tissue. The recombinant scAAV9 vector may be administered via spinal tap, e.g. to promote maximum targeting to CNS tissue, or intravenously, since the scAAV9 vector has the ability to cross the blood brain barrier. In certain embodiments, the recombinant scAAV9 vector preferably may be administered to the patient anytime until two months after mefloquine administration, depending on the clinical needs of the patient. Between $10^{10}$ to $10^{13}$ scAAV9 vectors may be administered depending on various factors, which could include the weight, age, sex, genetic makeup, and other medications of the patient.

According to Example 3, the administered recombinant scAAV9 vector will primarily transduce the patient's CNS tissue (particularly neurons and glial cells). Though the tropism of the scAAV9 vector is not perfectly directed to CNS tissue, expression may be limited to the patient's CNS tissue due to the CNS-specific promoter and enhancer constructs upstream of pfmdr1.

According to Example 3, the expression of pfmdr1 in CNS tissue will confer resistance to mefloquine as an efflux pump (e.g. as shown in FIG. 2), helping to prevent mefloquine from interacting with intracellular components of the CNS. Importantly, the specific expression of pfmdr1 in CNS tissue does not prevent mefloquine from desirably killing intracellular malaria, because infected non-CNS cells will generally lack pfmdr1 efflux pumps.

In this way, the method of Example 3 may prevent or reduce the severity of neuropsychiatric adverse effects of mefloquine medication. Additionally, this method may increase the concentration of mefloquine in the rest of the patient (outside of the CNS tissue), potentially increasing the desired medication efficacy.

The method of Example 3 may also reduce the side effects and increase the efficacy of antimalarial prophylaxis. For example during a mefloquine regimen of antimalarial prophylaxis, an adult may take 250 mg mefloquine once a week, beginning 1-3 weeks before travel to an area where malaria is epidemic, and continuing 4 weeks after travel ends. The neuropsychiatric side effects of mefloquine medication for prophylaxis may be similar to those resulting from mefloquine medication to clear a malaria infection.

According to Example 3, the administered recombinant scAAV9 vector will primarily transduce the patient's CNS, particularly neurons and glial cells. Hb9 promoter enhancer elements, and human synapsin 1 (SYN1) promoter will further restrict pfmdr1 expression to the patient's CNS tissue. Due to the vector tropism and tissue-specific promoter, liver cells (the first cell type that malaria infects), and red blood cells, will contain mefloquine for prophylactic efficacy. In this way, the method of Example 3 may prevent or reduce the severity of neuropsychiatric side effects of mefloquine prophylaxis, and may also increase the concentration of prophylactic mefloquine available in non-CNS tissues (e.g. liver and red blood cells).

Example 4—Two Different Tissue-Specific Vectors and Tissue-Specific Promoters

*Chlamydia trachomatis* is an intracellular bacterial pathogen that may cause blindness. *C. trachomatis* has many serotypes, some of which are tissue-specific. For example, the A, B, and C serotypes are specific to the eye, and the D, E, F, G, H, I, J, and K serotypes are specific to the genitalia and reproductive systems of men and women. The method of Example 4 takes advantage of the tissue-specificity of these serotypes of *C. trachomatis*, to provide antibiotic resistance in uninfected tissues.

The method of Example 4 may improve the treatment of intracellular, tissue-specific bacterial infections, like the D-K serotypes of *C. trachomatis*. Example 4 also demonstrates an embodiment of the present invention in which two different vector-promoter combinations are used to induce expression of an antimicrobial resistance gene primarily in two tissues.

As a first vector, a replication incompetent herpes simplex virus-1 (HSV1) vector containing a mefE gene downstream of the neural-specific SYN promoter, may be administered to the patient. As a second vector, an adeno-associated virus serotype 6 (AAV6) vector containing mefE downstream of a cardiac-specific α-myosin heavy chain promoter, may also be administered to the patient. For example, the recombinant vectors (AAV6 and HSV) preferably may be administered intravenously to the patient 6 hours before administration of azithromycin. However, the recombinant vectors may alternatively be administered intravenously between one month before and one week after azithromycin, depending on the clinical needs of the patient. In certain embodiments, between $10^{10}$ to $10^{13}$ HSV vectors, and $10^{10}$ to $10^{13}$ AAV6 vectors may be administered depending on various factors, which could include the weight, age, sex, genetic makeup, and other medications of the patient.

According to Example 4, the two recombinant vectors may be administered at different times. For example, the HSV vector may be administered 6 hours before antibiotic treatment, while the AAV6 vector may be administered 2 weeks before antibiotic treatment. The administered HSV vector will tend to transfect the patient's neural cells, primarily inducing expression of mefE in neurons due to the neural-specific SYN promoter. Meanwhile, the AAV6 vector will primarily induce expression of mefE in cardiac tissue.

According to Example 4, mefE will pump the azithromycin out of the patient's cardiac and neural tissues and into the extracellular space (e.g. as shown in FIG. 2). Hence, the method of Example 4 may increase the effective concentration of azithromycin to which *C. trachomatis* is exposed, and may reduce the incidence and severity of azithromycin's side effects in neural and cardiac tissue (that arise from interactions with azithromycin inside the patient's cells).

Figure 3:
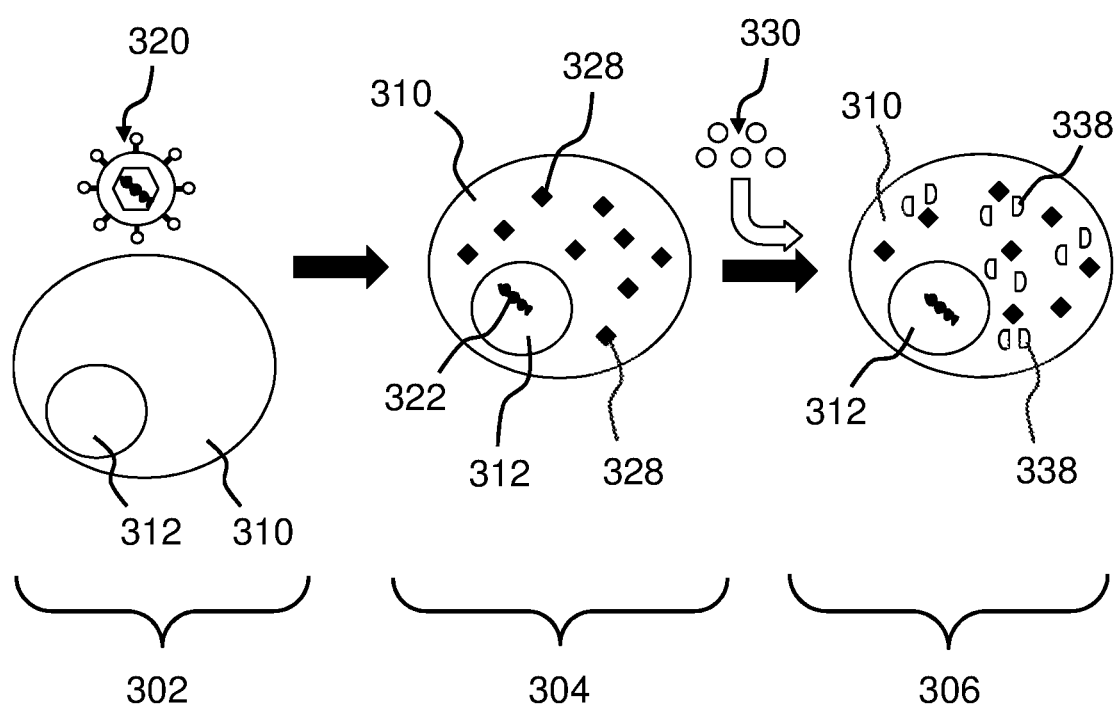
FIG. 3 schematically depicts a microscopic view of another exemplary embodiment of the present invention.

FIG. 3 schematically depicts a microscopic view of another exemplary embodiment of the present invention. In step 302, upon administration to the patient, a viral vector 320 containing a recombinant promoter and antimicrobial resistance gene will transfect the patient's eukaryotic cell 310. The nucleic acid 322, which in this embodiment codes for an antimicrobial resistance enzyme and promoter, then translocates to the nucleus of the patient's eukaryotic cell 312 and is converted into expressible double stranded DNA (dsDNA). However, the promoter and antimicrobial resistance gene that codes for an antimicrobial resistance enzyme may not be converted into dsDNA, if they are coming from a vector whose genome is dsDNA.

In step 304 of the embodiment of FIG. 3, the antimicrobial resistance gene in the transduced nucleic acid 322 is transcribed and translated, resulting in antimicrobial resistance enzyme 328 being present in the patient's eukaryotic cell 310.

In step 306 of the embodiment of FIG. 3, an antimicrobial agent 330 is administered to the patient. The antimicrobial agent 330 (e.g. administered to combat a microbial infection or for prophylaxis) may be administered before, at the same time as, or after the administration of the viral vector 320. In the embodiment of FIG. 3, the antimicrobial resistance enzyme 328 will enzymatically cleave the antimicrobial agent 330 in the patient's eukaryotic cell 310, creating a cleaved antimicrobial agent 338 that does not harmfully interact with internal components of the patient's eukaryotic cell 310. In certain embodiments, this may decrease adverse side effects of the antimicrobial agent 330 to the patient's eukaryotic cells, and may enable the use of an otherwise toxic antimicrobial agent to be safely administered to the patient.

Example 5—Antibiotic Combination, One Tissue-Specific Vector with Two Antimicrobial Resistance Genes The method of Example 5 may improve the treatment of extracellular bacterial infections, like *Staphylococcus aureus*, with an antimicrobial combination like quinupristin and dalfopristin. In example 5, a third generation, i.e. gutless, HAdV-11 adenovirus vector, containing both the vgb and ermA antimicrobial resistance genes, each downstream of a GAPDH promoter, is administered to the patient. For example, between $10^{11}$ to $10^{14}$ adenovirus vectors may preferably be administered intravenously depending on various factors such as the weight, age, sex, genetic makeup, and other medications of the patient.

In Example 5, quinupristin and dalfopristin are administered to the patient, for example at the amount and frequency according with current medical practices surrounding *S. aureus* infection. The recombinant adenovirus vector may be administered intravenously to the patient before, at the same time as, or after the quinupristin and dalfopristin antimicrobial medication. For example, the recombinant HAdV-11 vector preferably may be administered between one month before and one day after the quinupristin and dalfopristin medication, depending on the clinical needs of the patient.

In Example 5, the administered adenovirus vector will transduce eukaryotic cells of the patient, thus inducing expression of both vgb and ermA. ErmA will pump both quinupristin and dalfopristin out of eukaryotic cells, and into the extracellular space where *S. aureus* resides. Vgb will tend to cleave the quinupristin and dalfopristin (e.g. as shown in FIG. 3) that is not pumped out of the cell by ermA (e.g. as shown in FIG. 2), rendering it metabolically not harmful. The method of Example 5 may increase the effective concentration of quinupristin and dalfopristin to which *S. aureus* is exposed, and may also reduce the incidence and severity of the side effects of quinupristin and dalfopristin side effects, like joint and muscle aches, nausea, and hyperbilirubinemia, which arise from interactions with quinupristin or dalfopristin inside eukaryotic cells of the patient.

Figure 4:
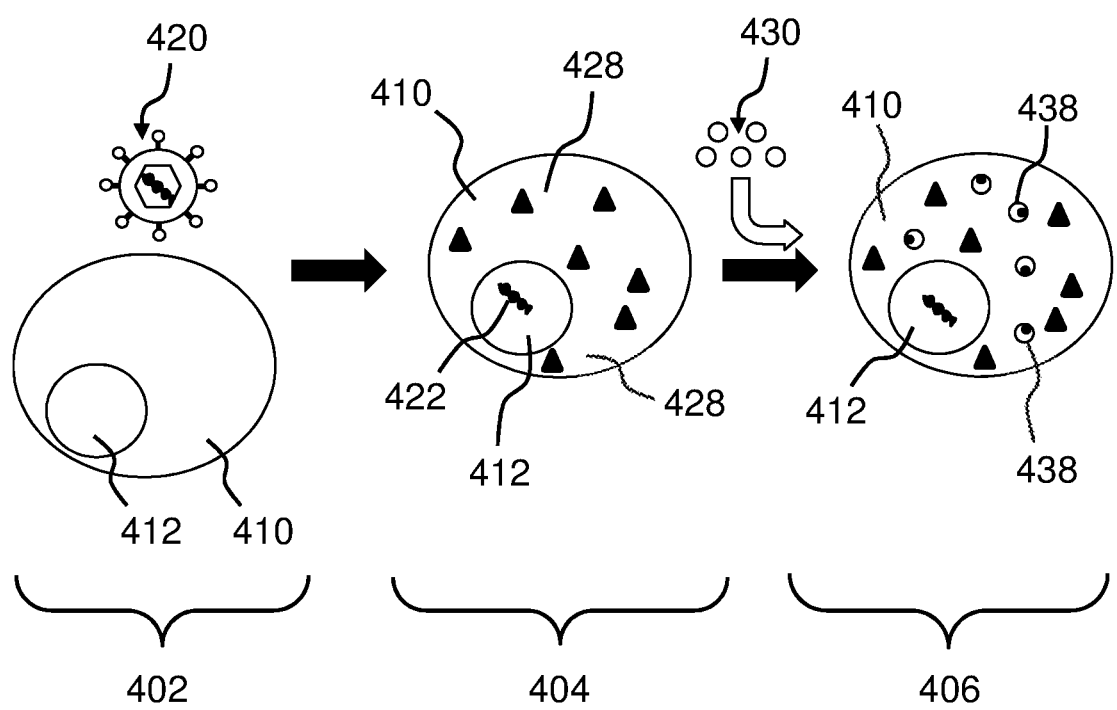
FIG. 4 schematically depicts a microscopic view of another exemplary embodiment of the present invention.

FIG. 4 schematically depicts a microscopic view of another exemplary embodiment of the present invention. In step 402, upon administration to the patient, the viral vector 420 containing a recombinant promoter and antimicrobial resistance gene will transfect the patient's eukaryotic cell 410. The nucleic acid 422, which in this embodiment codes for an antimicrobial resistance enzyme and promoter, translocates to the nucleus 412 of the patient's eukaryotic cell and is converted into expressible double stranded DNA (dsDNA). However, the promoter and antimicrobial resistance gene that codes for an antimicrobial resistance enzyme may not be converted into dsDNA, if they are coming from a vector whose genome is dsDNA.

In step 404 of the embodiment of FIG. 4, the antimicrobial resistance gene in the transduced nucleic acid 422 is transcribed and translated, resulting in an antimicrobial resistance enzyme 428 being present in the patient's eukaryotic cell 410.

In step 406 of the embodiment of FIG. 4, an antimicrobial agent 430 is administered to the patient. The antimicrobial agent 430 (e.g. administered to combat a microbial infection or for prophylaxis) may be administered before, at the same time as, or after the administration of the viral vector 420. In the embodiment of FIG. 4, the antimicrobial resistance enzyme 428 will modify (e.g. deaminate, oxygenate, phosphorylate, acetylate, etc.) the antimicrobial agent 430 in the patient's eukaryotic cell 410, so that it will not harmfully interact with the internal components of the patient's eukaryotic cell 410. In certain embodiments, this may decrease adverse side effects of the antimicrobial agent 430 to the patient's eukaryotic cells, and may enable the use of an otherwise toxic antimicrobial agent to be safely administered to the patient.

Example 6—Whole Organism Targeting Vector with Toxic Antimicrobial

Certain embodiments of the present invention may allow for the treatment of microbial infections with antimicrobials that would otherwise be toxic. For example, the method of Example 6 may allow for the treatment of antibiotic resistant extracellular bacterial infections, like MRSA, with an antibiotic agent that is not typically suitable for in vivo administration due to its toxicity (e.g. blasticidin S).

According to Example 6, a first generation adenovirus vector from the HadV-5 serotype that encodes the bsr gene downstream of a CMV promoter may be administered to the patient. For example, the recombinant vector may be administered intravenously to the patient before, or at the same time, as blasticidin S. In certain embodiments, the recombinant vector preferably may be administered to the patient 6 hours before administration of blasticidin S, but it may also be administered between one month before or at the same time as blasticidin S, depending on the clinical needs of the patient. In certain embodiments, $10^{11}$ to $10^{14}$ adenovirus vectors may be administered to the patient, depending on various factors such as weight, age, sex, genetic makeup, and other medications being administered.

According to Example 6, the administered adenovirus vectors will transduce the eukaryotic cells of patient. Expression of the bsr gene in each transduced cell will confer resistance to blasticidin S by modifying it (e.g. as shown in FIG. 4) into deaminohydroxyblasticidin S, which is not harmful within the eukaryotic cell.

According to Example 6, because the HAdV-5 vector does not transduce the MRSA, and the CMV promoter is specific for human cells, bsr will only be expressed in the human eukaryotic cells. That may significantly reduce the risk of blasticidin S resistance developing in the MRSA. Furthermore, because blasticidin S is not presently used in human patients, MRSA is not currently resistant to blasticidin S treatment. Hence, the blasticidin S that enters MRSA will more effectively kill the pathogenic microbes, while the blasticidin S that enters transduced human eukaryotic cells will be deactivated by blasticidin S deaminase. In this way, the method of Example 6 may provide for the clearance of antibiotic resistant pathogenic bacteria, while potentially inhibiting the damage that the otherwise-toxic antibiotic agent may have caused to the host.

Example 7—Tet Inducible Promoter and Antibiotic Agent

In certain embodiments of the present invention, an inducible promoter may be used to control expression of an antimicrobial resistance gene. Example 7 uses the inducible promoter tetracycline on (TetOn) construct, which is constitutively off, except in the presence of tetracycline. By using this inducible promoter construct, the expression of the antibiotic resistance gene may be regulated by administration of the antimicrobial agent tetracycline. According to Example 7, the antibiotic resistance gene downstream of the TetOn inducible promoter construct will encode resistance to tetracycline, so that upon treatment with tetracycline, transfected cells with the promoter-gene construct will become resistant to tetracycline.

The method of Example 7 may be applied to the treatment of Escherichia coli infection. A third generation lentivirus vector from HIV-1, containing the tetX gene downstream of the TetOn inducible promoter construct may be administered to the patient. In certain embodiments, the vector may be pseudotyped to the hepatitis C virus, to make enhance transduction for cells in the patient's liver. In certain embodiments, between $10^9$ and $10^{12}$ lentivirus vectors may be administered to the patient, depending on various factors such as patient weight, age, sex, genetic makeup, and other medications being administered. In certain embodiments, the recombinant lentivirus vector may be administered intravenously anytime before, until two days after, the tetracycline, depending on the clinical needs of the patient.

In Example 7, the administered lentivirus vector will transduce liver cells of the patient, thus inducing expression of tetX. TetX codes for a cytosolic enzyme that chemically modifies (e.g. as shown in FIG. 4) tetracycline to render it less harmful to eukaryotic cells of the patient. In this way, the method of Example 7 may reduce the incidence and severity of tetracycline's side effects on the patient (e.g. fatty liver, hepatic dysfunction, and acute liver failure) that may arise from interactions with tetracycline inside the patient's liver cells, while still allowing for the effective killing of pathogenic *E. coli.*

Certain embodiments of the present invention may be performed in mice or other mammals by adjusting the promoters and vectors to be murine or mammalian specific respectively.

Example 8—Two Vectors (One Tissue-Specific and One Whole Organism), and Toxic Antimicrobial Agent The method of Example 8 may allow for the treatment of antifungal resistant extracellular fungal infections, like *Cryptococcus neoformans*, with antifungal agents that are not otherwise suitable for in vivo administration due to their toxicity. The method of Example 8 employs a combination of vectors that may confer extra resistance to a particular tissue, while still providing resistance to the entire host.

In the method of Example 8, a Venezuelan equine encephalitis virus vector, which can infect murine cells, containing a hph gene downstream of the ubiquitous murine ROSA promoter, is administered to a patient (for example, administered to a mouse). An influenza hemagglutinin pseudotyped equine infectious anemia virus vector, which is pulmonary-specific, containing a hph gene downstream of the pulmonary-specific murine SP-C promoter, is also administered to the same patient. The recombinant vectors may be administered intravenously, such as by tail vein injection, to the patient anytime before hygromycin B administration up until the time of hygromycin B administration. For example, between $10^9$ and $10^{13}$ alphavirus vectors, and between $10^8$ and $10^{12}$ lentivirus vectors may be administered to the patient, depending on various factors such as the mouse's weight and genetic makeup.

According to Example 8, the administered recombinant vectors will transduce eukaryotic cells of the patient. Expression of the hph gene in each transduced cell will confer resistance to hygromycin B by phosphorylating its 4' hydroxyl group (e.g. consistent with FIG. 4), thereby turning it into 7'-O-phosphoryl-hygromycin B, which is not harmful. As neither of the recombinant vectors will transduce *C. neoformans*, and both the murine ROSA and SP-C promoters are specific for murine cells, hph will only be expressed in the murine cells, preventing hygromycin B resistance from developing in *C. neoformans.*

Furthermore, administration of the recombinant vector combination according to Example 8 may allow for extra hygromycin B protection to be conferred to the lungs, in addition to the standard protection conferred to the rest of the patient's body. Such extra protection may derive from an increased percentage of pulmonary cells that are transduced with the resistance gene, and an increase in the average number of transgenes that pulmonary cells receive relative to other cell types (which increases their expression level of hph). The hygromycin B that enters a murine cell transduced with hph will be deactivated by hygromycin B deaminase, whereas the hygromycin B that enters the *C. neoformans* will remain active, killing pathogenic microbes. Thus, the method of Example 8 may help clear pathogenic fungi while inhibiting damage that the otherwise-toxic antimicrobial agent might have caused to the patient.

In the foregoing specification, the invention is described with reference to specific exemplary embodiments, but those skilled in the art will recognize that the invention is not limited to those. It is contemplated that various features and aspects of the invention may be used individually or jointly and possibly in a different environment or application. The specification and drawings are, accordingly, to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

I claim:

1. A method to kill a pathogenic microbe in a patient, comprising:

transducing eukaryotic cells of the patient with a first viral vector that will not transfect the pathogenic microbe, the pathogenic microbe being an extracellular pathogenic microbe or a tissue-restricted pathogenic microbe, the first viral vector is replication defective and encodes in a recombinant genome of the first viral vector a first antimicrobial resistance gene and a first promoter operatively linked to the first antimicrobial resistance gene; and
administering an antimicrobial medication to the patient.

2. The method of claim 1 wherein the first antimicrobial resistance gene is a bsr gene, the first promoter is a CMV promoter, and the first viral vector is a human adenovirus vector serotype 5 that encodes the bsr gene downstream of the CMV promoter.

3. The method of claim 1 wherein the first viral vector is selected to primarily transduce one or more specific types of eukaryotic cells of the patient.

4. The method of claim 3 wherein the one or more specific types of eukaryotic cells of the patient belongs to the group consisting of neural, cardiac, skeletal, or pulmonary cells.

5. The method of claim 3 wherein the first viral vector is a self-complementary adeno-associated virus serotype 9 vector (scAAV9), with Hb9 promoter enhancer elements and a synapsin 1 (SYN1) promoter that are upstream of pfmdr1, that primarily transduces CNS tissue of the patient.

6. The method of claim 5 wherein administering the antimicrobial medication to the patient comprises mefloquine administration.

7. The method of claim 1 wherein the first viral vector is modified to primarily transduce one or more specific types of eukaryotic cells of the patient.

8. The method of claim 1 further comprising transducing the eukaryotic cells of the patient with a second viral vector that will not transfect the pathogenic microbe, the second viral vector encoding in a recombinant genome of the second viral vector a second antimicrobial resistance gene and a second promoter, the second viral vector being replication defective.

9. The method of claim 8 wherein the second promoter is the same as the first promoter.

10. The method of claim 8 wherein the second viral vector is chosen to primarily transduce one or more specific types of eukaryotic cells of the patient.

11. The method of claim 10 wherein the first viral vector is a lentivirus vector with a VSV-G pseudotype, and the second viral vector is an adeno-associated virus serotype 1 that primarily transduces skeletal muscle cells, cardiac muscle cells, and central nervous system cells of the patient.

12. The method of claim 10 wherein the patient is a mouse.

13. The method of claim 12 wherein the first viral vector is a replication incompetent Venezuelan equine encephalitis virus vector containing a hph gene downstream of a murine ROSA promoter and the second viral vector is a pulmonary-specific influenza hemagglutinin-pseudotyped equine infectious anemia virus vector containing a hph gene downstream of a murine PGK1 promoter.

14. The method of claim 13 wherein administering the antimicrobial medication to the patient comprises hygromycin B administration.

15. The method of claim 8 wherein the patient is a human, the first viral vector is a herpes simplex virus 1 vector containing a mefE macrolide resistance gene downstream of a neural-specific SYN promoter, and the second viral vector is an adeno-associated virus serotype 6 vector containing mefE downstream of a cardiac-specific α-myosin heavy chain promoter, and wherein administering the antimicrobial medication to the patient comprises azithromycin administration.

16. The method of claim 1 wherein the antimicrobial medication is an antibiotic medication, and the pathogenic microbe is a bacterium.

17. The method of claim 16 wherein the first viral vector is a human adenovirus serotype 35 vector, containing a human PGP gene downstream of a human EF-1 promoter.

18. The method of claim 17 wherein administering the antimicrobial medication to the patient comprises ciprofloxacin administration.

19. The method of claim 1 wherein the pathogenic microbe is a fungus, and the antimicrobial medication is an antifungal agent selected from the group consisting of azoles, polyenes, echinocandins, and flucytosine.

20. The method of claim 19 wherein the first viral vector is an adeno-associated virus serotype 1 vector containing a CDR1 antifungal resistance gene downstream of a synthetic CAG promoter.

21. The method of claim 20 wherein administering the antimicrobial medication to the patient comprises voriconazole administration.

22. The method of claim 1 wherein the antimicrobial medication is an antiparasitic agent, and the pathogenic microbe is a parasite.

23. The method of claim 1 wherein the first promoter is selected from the group consisting of ubiquitous promoters, tissue-specific promoters, inducible promoters, and synthetic promoters.

24. The method of claim 23 wherein the first viral vector is a HIV-1 lentivirus vector, containing a tetX tetracycline resistance gene downstream of a TetOn inducible promoter.

25. The method of claim 24 wherein administering the antimicrobial medication to the patient comprises tetracycline administration.

26. The method of claim 1 wherein the first viral vector is administered intravenously to the patient before the antimicrobial medication is administered to the patient.

27. The method of claim 1 wherein the first viral vector is a human adenovirus serotype 11 vector, containing both the vgb and ermA antimicrobial resistance genes, each downstream of a GAPDH promoter.

28. The method of claim 27 wherein administering the antimicrobial medication to the patient comprises quinupristin administration and dalfopristin administration.

29. The method of claim 1 wherein the antimicrobial medication is systemically administered to the patient.

* * * * *